United States Patent
Ray et al.

(10) Patent No.: US 10,902,534 B2
(45) Date of Patent: Jan. 26, 2021

(54) COGNITIVE TRAVEL ASSISTANCE

(71) Applicant: International Business Machines Corporation, Armonk, NY (US)

(72) Inventors: Shubhadip Ray, Secaucus, NJ (US); Andrew S. Christiansen, Dubuque, IA (US); Norbert Herman, Denver, CO (US); Avik Sanyal, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 321 days.

(21) Appl. No.: 15/909,607

(22) Filed: Mar. 1, 2018

(65) Prior Publication Data
US 2019/0272602 A1    Sep. 5, 2019

(51) Int. Cl.
*G06Q 50/14* (2012.01)
*H04L 29/08* (2006.01)
(Continued)

(52) U.S. Cl.
CPC ........... *G06Q 50/14* (2013.01); *G06F 16/285* (2019.01); *G16H 10/60* (2018.01); *H04L 67/306* (2013.01)

(58) Field of Classification Search
CPC ........... G06Q 30/0269; G06Q 30/0241; G06Q 30/0277; G06Q 30/0201; G06Q 50/14; G06Q 30/02; G06Q 10/10; G06Q 20/02; G06Q 2220/00; G06Q 30/0631; G06Q 50/01; G06Q 50/26; G06Q 10/00; G06Q 10/0631; G06Q 10/08; G06Q 30/0202; G06Q 40/02; G06Q 10/06; G06Q 10/063;
(Continued)

(56) References Cited

U.S. PATENT DOCUMENTS 8,732,101 B1 * 5/2014 Wilson ................ G06F 16/9535
706/15
9,009,167 B2    4/2015 Cerny
(Continued)

FOREIGN PATENT DOCUMENTS

| JP | 2002311158 A | 10/2002 |
|---|---|---|
| WO | 2016042282 A1 | 3/2016 |
| WO | 2016130232 A1 | 8/2016 |

OTHER PUBLICATIONS

"Vacation Planning? The Weather Channel Interactive Offers the ultimate Travel Planner on weather.com", Business Wire, May 8, 2007, 1 page, <https://www.businesswire.com/news/home/20070508005198/en/Vacation-Planning-The-Weather-Channel-Interactive-Offers-the-Ultimate-Travel-Planner-on-Weather.com> (Year: 2007).*

(Continued)

*Primary Examiner* — Jeff Zimmerman
*Assistant Examiner* — Jorge G Del Toro-Ortega
(74) *Attorney, Agent, or Firm* — Scott S. Dobson

(57) ABSTRACT

Data sources containing a plurality of health information is combined throughout a plurality of travelers. Profile vectors are created from each individual member of the traveling party and a group profile vector is built as a representative whole of the traveling parties interests. Potential travel destinations vectors are clustered and mapped with dimensions comprised in the group profile vector. A recommended vacation or travel destination itinerary is proposed based on the highest overlaying dimensional score between the group profile vector and potential travel destinations.

12 Claims, 5 Drawing Sheets

(51) Int. Cl.
*G16H 10/60* (2018.01)
*G06F 16/28* (2019.01)

(58) Field of Classification Search
CPC ............. G06Q 10/101; G06Q 20/3825; G06Q 20/3827; G06Q 20/3829; G06Q 20/385; G06Q 20/405; G06Q 30/0214; G06Q 30/0253; G06Q 30/0261; G06Q 30/0267; G06Q 40/00; G06Q 40/06; G06Q 40/08; G06Q 50/22

See application file for complete search history.

(56) References Cited

U.S. PATENT DOCUMENTS

| | | | |
|---|---|---|---|
| 2002/0091535 A1 | 7/2002 | Kendall et al. | |
| 2008/0059224 A1 | 3/2008 | Schechter | |
| 2008/0246629 A1 | 10/2008 | Tsui et al. | |
| 2009/0012799 A1 | 1/2009 | Hornthal et al. | |
| 2013/0036139 A1* | 2/2013 | Kung | G06Q 10/025 707/780 |
| 2013/0329881 A1* | 12/2013 | Fukuma | G06Q 10/02 379/265.12 |
| 2014/0059066 A1* | 2/2014 | Koloskov | G16H 40/63 707/758 |
| 2014/0324721 A1* | 10/2014 | Rennison | G06Q 50/2057 705/321 |
| 2015/0073841 A1 | 3/2015 | Gray et al. | |
| 2015/0356441 A1 | 12/2015 | Faith et al. | |
| 2016/0300252 A1* | 10/2016 | Frank | G06F 16/24578 |
| 2017/0039339 A1* | 2/2017 | Bitran | G16H 50/70 |
| 2017/0293851 A1* | 10/2017 | Chawla | G06Q 10/08 |
| 2018/0101800 A1* | 4/2018 | Lecue | G06F 16/24522 |

OTHER PUBLICATIONS

Mell et al., "The NIST Definition of Cloud Computing", National Institute of Standards and Technology, Special Publication 800-145, Sep. 2011, 7 pages.

"Vacation Planning? The Weather Channel Interactive Offers the Ultimate Travel Planner on weather.com", Business Wire, May 8, 2007, 1 page, <https://www.businesswire.com/news/home/20070508005198/en/Vacation-Planning-The-Weather-Channel-Interactive-Offers-the-Ultimate-Travel-Planner-on-Weather.com>.

* cited by examiner

COGNITIVE TRAVEL ASSISTANCE

BACKGROUND

The present disclosure relates to cognitive computing, and more specifically, to multi-source analytics.

SUMMARY

Aspects of the present disclosure are directed to a method that can generate and recommend an optimized vacation or travel destination and itinerary by combining one or more real-time data sources associated with a plurality of travelers. Combining data sources includes receiving a plurality of data where a first portion of the plurality of data is associated with a first classification, a second portion of the plurality of data is associated with a second classification, and a third portion of the plurality of data is associated with a third classification. The method can comprise building a personal profile vector for each individual traveler comprised in the plurality of travelers by weighting a plurality of vectors on a plurality of dimensions. The method can further comprise building a group profile vectors from the individual travelers comprised in the plurality of travelers by clustering the plurality of dimensions of the plurality of vectors based on a range of applied weighted values. The method can further retrieve travel destinations and environmental forecast factors and build destination profiles by mapping the dimensional compatibility of potential destination to the group profile vectors. The method can then output a recommended vacation or travel destination and itinerary to the one or more data sources and update the dimensions of the group profile vector based on traveler feedback.

Further aspects of the present disclosure are directed to a system comprising a computer readable storage medium storing a corpus of data, a user interface configured to receive input and present output and a processor communicatively coupled to the computer readable storage medium and the user interface and having a memory comprising instructions. When executed by the processor, the processor can combine data sources comprising a plurality of data where a first portion of the plurality of data is associated with a first classification, a second portion of the plurality of data is associated with a second classification, and a third portion of the plurality of data is associated with a third classification. The processor can further be configured to build a personal profile vector for each individual traveler comprised in the plurality of travelers by weighting a plurality of vectors on a plurality of dimensions. The processor can further be configured to build a group profile vector from the individual travelers comprised in the plurality of travelers by clustering the plurality of dimensions of the plurality of vectors based on a range of applied weighted values. The processor can further retrieve travel destinations and environmental forecast factors and build destination profiles by mapping the dimensional compatibility of potential destination to the group profile vectors. The processor can then output a recommended vacation or travel destination and itinerary to the one or more data sources and update the dimensions of the group profile vector based on traveler feedback.

Further aspects of the present disclosure are directed towards a computer program product for generating and recommending an optimized vacation or travel destination and itinerary. The computer program product can comprise a computer readable storage medium having program instructions embodied therewith and executable by a processor to cause the processor to combine data sources comprising a plurality of data where a first portion of the plurality of data is associated with a first classification, a second portion of the plurality of data is associated with a second classification, and a third portion of the plurality of data is associated with a third classification. The program instructions can build a personal profile vector for each individual traveler comprised in the plurality of travelers by weighting a plurality of vectors on a plurality of dimensions. The program instructions can further build a group profile vector from the individual travelers comprised in the plurality of travelers by clustering the plurality of dimensions of the plurality of vectors based on a range of applied weighted values. The program instructions can retrieve travel destinations and environmental forecast factors and build destination profiles by mapping the dimensional compatibility of potential destination to the group profile vectors. The program instructions can then output a recommended vacation or travel destination and itinerary to the one or more data sources and update the dimensions of the group profile vector based on traveler feedback.

BRIEF DESCRIPTION OF THE DRAWINGS

The drawings included in the present application are incorporated into, and form part of, the specification. They illustrate embodiments of the present disclosure and, along with the description, explain the principles of the disclosure. The drawings are only illustrative of certain embodiments and do not limit the disclosure.

Figure 1:
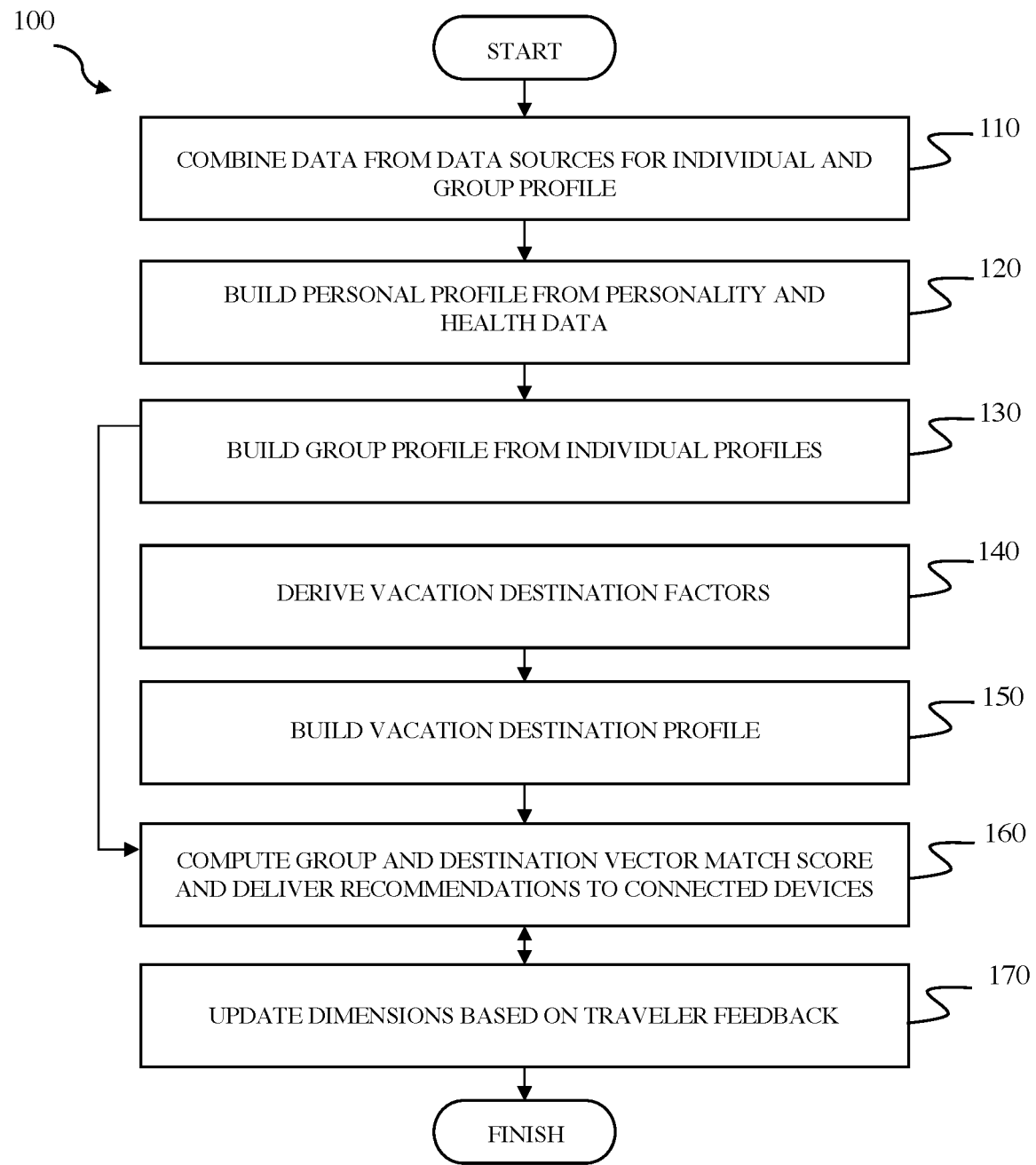
FIG. 1 illustrates a flowchart of an example method for identifying a travel plan and destination in accordance with some embodiments of the present disclosure.

While the present disclosure is amendable to various modifications and alternative forms, specifics thereof have been shown by way of example in the drawings and will be described in detail. It should be understood, however, that the intention is not to limit the present disclosure to the embodiments described. On the contrary, the intention is to cover all modifications, equivalents, and alternatives falling within the spirit and scope of the present disclosure.

DETAILED DESCRIPTION

Aspects of the present disclosure relate to multi-source analytics. More particular aspects relate to a planner system configured to cluster weighted ratios between preference vectors and traveler dimensions with predictive geological data. A travel itinerary is then derived for a traveling party based on compatibility results. A derived travel itinerary can provide a summative representation of a plurality of information. The summative representation reflects the location and itinerary plan with the highest mapped compatibility score in consideration to potential underlying effects a destination can impose based on traveler medical information (e.g., health), forecasted external factors (e.g., weather, environmental conditions), and applied travel methods (e.g., car, plane, boat). Although not limited to such applications, an understanding of some embodiments of the present disclosure may be improved given the context of multi-source analytics.

Aspects of the present disclosure relate to a multi-source analytics system for travelers planning a trip (e.g., vacation). Using analytics from machine learning systems, some embodiments of the present disclosure can be configured to analyze the impact of weather and environmental conditions of a possible vacation destination on the health of an individual traveler, group of travelers (e.g., family), and/or a combination of both, herein referred as the traveling party.

Some embodiments of the present disclosure relate to cognitive computing and artificial intelligence, and more specifically, cognitive health models. Cognitive health models can extrapolate data from a traveler's medical history and perform simulations based on future events. In embodiments, an example cognitive health model is WATSON HEALTH™ of IBM®. Although not limited to such cognitive health model, an understanding of some embodiments of the present disclosure may be improved given the context of the cognitive health model. Additionally, some embodiments of the present disclosure relate to rule-based machine learning and weather impact models. Rule-based machine learning identifies, learns, or evolves rules to store, manipulate, or apply. Machine learning weather impact models identify and extract environmental data (e.g., temperature, humidity, wind) and output hyper-local forecasts. Environmental data can be a plurality of historical weather inputs comprised in databases such as, but not limited to, the WEATHER COMPANY database.

Some embodiments relate to devices in the Internet of Thing (IoT). The IoT can be a network of physical devices generating and sharing data. Physical devices can be, but are not limited to, information processing devices (e.g., computers, laptops, desktops, etc.), medical devices (e.g., diabetes monitor, hearing aids, heart monitor), consumer devices (e.g., mobile phones, tablets, handheld devices, wearable devices, etc.), and other devices having electronics, hardware, software, sensors, actuators, and/or network connectivity.

Travelers tasked with planning a vacation can find difficulties in accommodating for all variables that may induce un-favoring health implications to individuals. However, this task becomes even more cumbersome when travelers unknowingly have an undiagnosed health condition. Without any symptoms or cause for concern, a traveler has very little reason to believe they possess an underlying condition. As such, a traveling party could mistakenly travel to a destination in which, with the combination of geological factors (e.g., high altitude) and the underlying condition (e.g., sleep apnea), trigger dangerous symptoms (e.g., breathing cessation) associated with the undiagnosed condition.

Having access to traveler health and real-time vital data as well as the environmental forecast conditions for a given location over the next twelve months, can help evaluate the risk of traveling to a destination if an underlying condition were to be predicted. Advantageously, the present disclosure improves the accuracy and efficiency of planning a vacation using medical information and personal preferences to establish a compatibility score for potential travel destination profile vectors and accompanied itinerary plans. Giving weighted values towards dimensions (e.g., health information, requests) and using the assistance of predictive analytics machine learning programs (e.g., WATSON HEALTH™), the planner system can identify and recommend the highest mapped compatible location and travel itinerary for a traveling party with consideration towards their personality, preferences, and health. For example, if a family wishes to find a new vacation destination, the traveler tasked with planning the trip will need to ensure that the travel arrangements and predictive environmental conditions are acceptable for all participating family members.

As another example advantage, aspects of the present disclosure improve the functioning of a computer by optimizing a computer to identify and match identical-vector data (e.g., health services, social media, web-based messages, device) between a traveling party and potential vacation or travel destinations faster and more efficiently than traditional methods. This results in a savings of computational resources such as CPU and memory.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. In particular, the terms "present invention" or "invention," as used herein, is used to refer to examples or embodiments of the concepts described in this detailed description. The detailed description is to be construed as exemplary only and does not describe every possible embodiment of the invention.

Referring now to the figures, FIG. 1 depicts a flowchart of an example method 100 for cognitive travel assistance, and more specifically, computing a health risk or correlating conditions based on monitored health data in accordance with some embodiments of the present disclosure. A travel destination can then be calculated based off a location that mitigates the highest amount of risk. In various embodiments, the method 100 can be implemented by one or more processors. In embodiments, the method 100 starts with operation 110. Operation 110 can receive health information data from, for example, a plurality of data sources relating to members of a traveling party. In embodiments, health information can comprise medical information (e.g., a history of patient clinical information, prescriptions, known issues) psychological information (e.g., personality, fears, interests, phobias) and biological information (e.g., age, weight). In embodiments, a plurality of data sources can comprise vectors such as, but not limited to, health services (H) (e.g., diagnosed issues, prescriptions, allergies), social media (SM) (e.g., pictures, posts), web-based messages (M) (e.g., texts, emails), and wearables (W) (e.g., smart watches). In embodiments, members of a traveling party can comprise an individual, a group, a family, and any combination thereof. Operation 110 proceeds to aggregate the relative health information data from the plurality of data sources to account for the average health of the traveling party and any periodic or intermittent conditions that may be prevalent. Relative health information collected via wearables can be collected from previously documented physical examinations as well as in real-time. Operation 110 stores the newly collected health information data from data sources in an isolated database connected to a network system containing the individual profiles of the traveling party's members.

Using machine learning models and natural language processing, traveler information is extracted from the isolated database in operation 110. For example, parse dependency trees are used to learn the context of the relevant data, their semantic type, and their semantic relationship. Operation 120 then builds personal profile vectors for each individual comprised in the plurality of travelers based on the traveler's health information. Personal profile vectors are held in storage until further use.

For a given individual traveler (P), a profile vector is computed and mapped to a traveler cluster through k-means clustering algorithms comprising function components. K-means clustering is a method of vector quantization aimed to partition a set of data (e.g., the set of data stored in the isolated database) into a set of meaningful k-cluster subclasses (e.g., profile vectors).

In embodiments, profile vectors operate on a one-dimensional array of data and the functional components ($f_1, f_2, f_3$) (e.g., attributes) receive all information relating to an individual's health and personality. Given the initial set of data from the traveling party, the algorithm begins the initialization phase. Using random partition, attributes are clustered using self-learning rules and proceed through alternating assignment and updating steps. Each cluster data point is assigned to a profile vector with the closest related Euclidean distance. New means are then calculated to be the centroids of the data points. In embodiments, $f_1$ acts upon health services ($f_1(H)$). Information such as, but not limited to, diagnosed medical issues, psychological evaluations, prescriptions, age, weight and height are parsed from multiple medical practitioner databases (e.g., personal medical files) as well as self-reported by a traveler. Social media and messages comprise $f_2$ ($f_2$ (SM+M)). Correlating social media profiles of the individual traveler are analyzed with natural language processors to retrieve additional data points for a given person. In embodiments, data points can comprise, but are not limited to, personality type, fears, phobias, motivation, and estimated undiagnosed health issues. For example, a social media post may illustrate a traveler atop a cliff with the caption, "Nervous but excited!" The machine learning cognitive model may insinuate a minor fear of heights and the symptom nervousness, yet, infer a willingness to try the action again based on a positive response. Information obtained from wearable devices comprises $f_3$ ($f_3$ (W)). Wearable devices, both consumer and medical, can provide data comprising but not limited to, heart rate and breathing levels to be incorporated into the profile.

In embodiments, the algorithm for computing a profile vector for a given individual ($V_p$) can be represented as $$P=f_p(H,SM,M,W)=f_1(H)+f_2(SM+M)+f_3(W)=V_p[\text{dimensions}]$$

where $f_p$ is a function derived from functions $f_1$, $f_2$, and $f_3$. $V_p$ represents the profile vector output. Using predictive clustering, the algorithm establishes weight ratios for the different dimensions of the vector. In embodiments, the output profile vector comprises a plurality of dimensions established by categorizing inputs of the function and assigning adjustable weights based on applications and data semantics of each personality. Both types of clustering mentioned are provided by way of example only for purposes of explanation but are not to be construed as limiting. In embodiments, weights and biases can be pre-set by traveler preference and/or deduced by the machine learning system based on traveler feedback. In embodiments, dimensions can comprise categories relating, but are not limited to, adventurous, allergies, blood pressure, personality type, cholesterol level, and sea sickness and nausea susceptibility. The weights for each vector dimension may be pre-configured for the first few runs of the method based on the importance of each vector dimension to a travel cluster. Overtime, in embodiments, the weights can be adjusted in future runs based on collected traveler feedback.

Given the data for P in operation 120, a profile for the plurality of travelers ($P_1, P_2, P_3$) forming the traveling party (G) is established in operation 130. The traveling party profile vector will be a vector V, in the same dimensions and any additional dimensions significant to be considered for an individual member established in operation 120. In embodiments, the formula for computing a profile vector of the traveling party ($V_G$) can be represented as $$G=f_G(P_1,P_2,P_3)=V_G[\text{dimensions}]$$

where the dimensions must include at least all dimensions categorically assigned in operation 120. In embodiments, dimensional categories for the traveling party such as, but not limited to, blood pressure and heart rate, can be best represented by a range of values comprising the minimum and maximum values of all the travelers in a group. In embodiments, dimensional categories for the traveling party such as, but not limited to, personality type and nausea susceptibility, can be best represented as an average value. In operation 130, the clustering algorithm clusters the traveling party's profile, as was done in operation 120 with personalities, and applies weights and biases to each dimensional category within a range relative to the corresponding dimensions.

Using analytics from predictive weather services and other repositories of environmental condition providers and more specifically historical weather data inputs, operation 140 profiles potential destination factors based on the forecast of the weather and environment. Information obtained in operation 140 is pulled for a predetermined historical time range using predictive analytics. In embodiments, predictive analytics are used to make predictions about unknown future events (e.g., thunderstorms, rain, hail). Predictive analytics uses many techniques from data mining, statistics, modeling, machine learning, and artificial intelligence to analyze current data to make predictions about the future. Patterns found in historical and transactional data can be used to identify risks and opportunities for the future. Predicative analytics models capture relationships among many factors to assess risk with a particular set of conditions to assign a score or by weightage.

For example, in embodiments, an estimation for the next 12 months' weather and environment profile is established for an originally requested destination. The forecasted weather and environment profile is compiled from analytics information comprising humidity (HU), altitude (A), barometric pressure (BP), temperature (T), precipitation (P), and academic research (AR). The given travel mode may provide complications to some members of the traveling party. In addition to using predictive analytics for a weather and environmental profile, analytics are used to determine an optimal travel mode, method, and path with the least related health related ramifications. The analytics used comprise, but are not limited to, travel time (TT), available mobility of travelers (MO), surroundings (SD), and available cuisine (C). Using data and the predictive machine-learning analysis programs, information relating to a destination request is computed to determine if any potential health risk occur that may trigger a symptom of a reported health issue. Data points used comprise, but are not limited to, health issues (I), symptoms (S), symptom triggers (ST), probability of occurrence (O), and medication available (MA). Separate, but similar to the clustering algorithms of operation 120 and operation 130, vacation destination factors (VD) are weighted, computed and represented as $$VD = f_{VD}(HU, A, BP, T, P, AR) = V_{VD}[\text{dimensions}]$$

where $V_{VD}$ is a vector in the different dimensions. The dimensions in the vector $V_{VD}$ can be over a variable range of time. For example, for vacations planned well in advance, the range can be a time period of six months to one or more years. On the contrary, for vacations planned with a short lead time, the range could be a time period of a few days, with more recent time blocks and smaller subsets (e.g., next week) taken and analyzed more accurately.

Operation 150 uses the results of vector $V_{VD}$ and builds a vacation destination profile. The vector $V_{VD}$ is mapped based on clusters. Together, each cluster creates a permissible health vector to the vacation destination profile vector ($VDP_{VD}$) in like dimensions. In doing so, the traveling party vector is optimized to find the highest potential matched locations. In embodiments, mapping considers conditions and diseases that may flare up under certain weather or environmental conditions and uses preset rules to generate more rules from runs of the algorithm, machine-learning health services and other sources. For example, a traveler with a dry skin problem will be more affected by areas with low humidity, whereas a traveler with asthma will be more affected by areas with high humidity from the increased amount of mold. As a result, destination profiles comprising an average humidity dimension will be assigned the highest weight.

Operation 160 clusters the dimension of the profile vector for a traveling party from the results of operation 130 and with a permissible health vector of the possible vacation destinations ($VDP_{VD}$) from operation 150. Every overlaying mapped dimension is assigned a value of 1 and misaligned dimensions are assigned a value of 0. The final mapped score calculated per traveling group/destination combination ($G-V/V_G-VDP_{VD}$) is the addition of the counts (e.g., 1's and 0's from each dimension) for all the dimensions. A monthly valuation for a vacation destination itinerary with similarity to an ideal destination itinerary is given based upon the number of applicable dimensions. For example, if 10 dimensions are clustered, the output monthly valuation would range from 0-10, whereas 10 would represent the optimal destination based on the permissible health vector of the destination compared to the health vector of the traveling party. The destination with the highest valuation is recommended to the traveling party.

In embodiments, a recommendation further considers, identifying and predicting undiagnosed conditions from the plurality of data and suggesting alternative means and available medicine best suited to provide maximum mitigation without affecting the majority of the traveling party or imposing significant health implications towards individuals. For example, a wearable device may recently identify an abnormality in the number of completed REM sleep cycles a traveler achieves per night. While a traveler may be aware they are tired, the traveler may often mistakenly justify tiredness as direct result from an exhaustive work week. However, coupled with the travelers previously documented records of a dry mouth, the system can predict the traveler has sleep apnea. The system can then further recommend travel instructions and medical safety instructions to follow as well as additional supplies that would help alleviate or account for any detrimental issues if they were to arise.

A mapped recommendation can be further computed by incorporating the traveling party's financial situation and their willingness to travel within their means as well as a surprise factor. A surprise factor considers the traveling parties potential motivation or interest for selecting a given destination and analytics derived from current events at a destination. For example, a traveling party may select Park City, Utah for the skiing and this method may recommend other cities, such as Vail, Colo., or Sun Valley, Id. Depending on the adventurousness and thrill-seeking factors of a traveling party profile vector, the surprise factor may highlight lesser-known destinations or activities such as Jackson Hole, Wyo., where real-time sales analytics indicate a sale on lift tickets and snowmobiling tours. The recommendation and accompanied information (e.g., medicine, packing list) is sent to the plurality of data sources (e.g., smart watches, mobile phones, computers) comprised in the traveling party, ready for approval.

Based on analyzed social media data, survey feedback and vacation travel data for traveler clusters in previously executed recommendations, self-learning rules in operation 170 derives updated weights for each dimension of the vectors for computing the compatibility score. The weights on the dimensions may be adjusted, if needed, and operation 170 updates rules between the group profile vector and the destination profile vector as to establish an ideal travel destination profile vector of a future recommendation of a traveling party vector. Thus, the algorithm clusters the group profile vector and destination profile vectors to generate rules for self-learning. Overtime additional dimensions can also be added to the vectors based on feedback from vacationers, survey data, and changing circumstances.

It is noted that FIG. 1 is intended to depict the representative major operations of an example method 100 for cognitive travel assistance. In some embodiments, however, individual operations can have greater or lesser complexity than as represented in FIG. 1, operations other than or in addition to those shown in FIG. 1 can be present, and the number, type, and configuration of such operations can vary.

Figure 2:
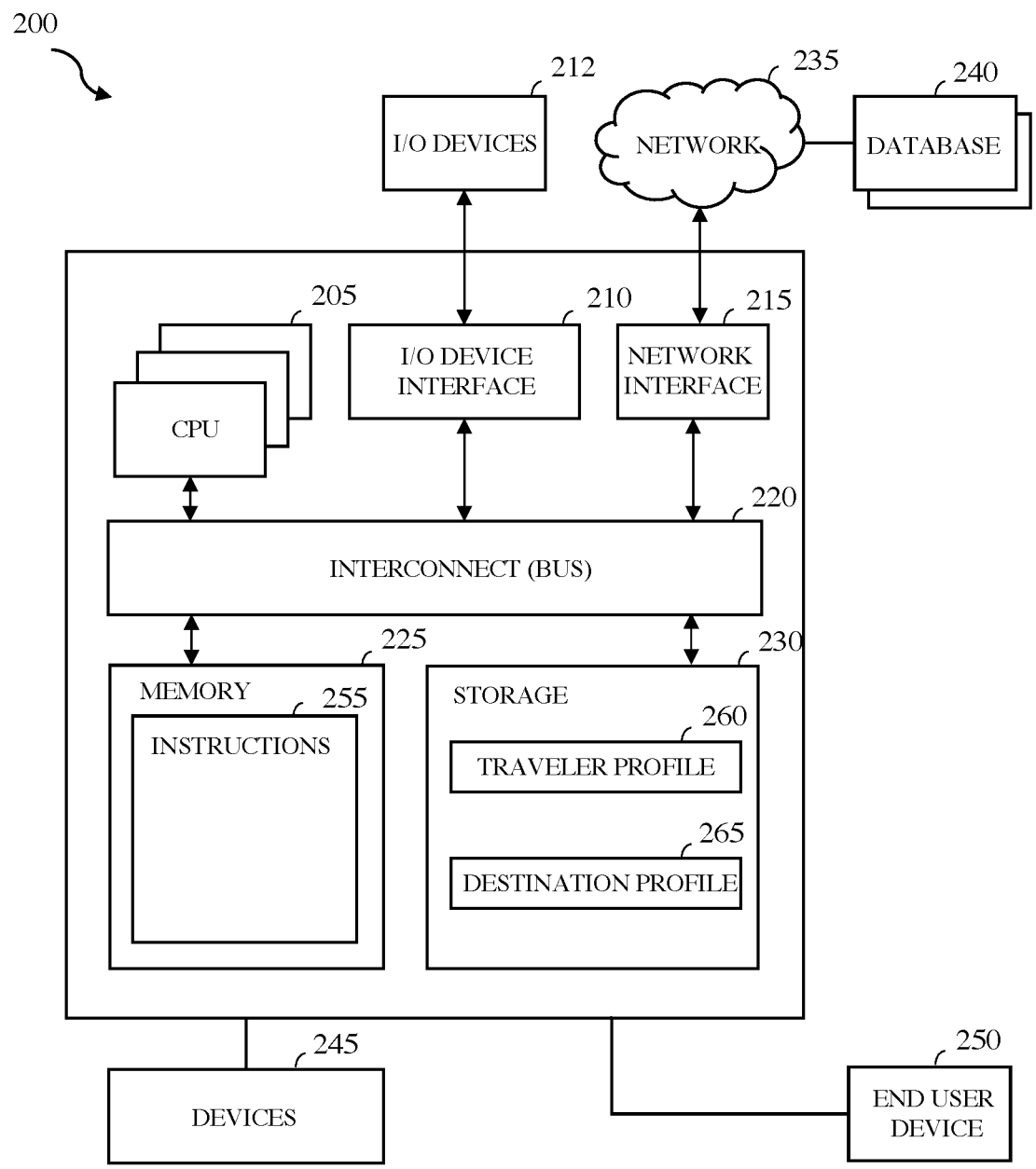
FIG. 2 illustrates a block diagram of an example travel assistance system in accordance with some embodiments of the present disclosure.

FIG. 2 illustrates a block diagram of an example travel assistance system 200 in accordance with some embodiments of the present disclosure. In some embodiments, travel assistance system 200 is consistent with embodiments method 100 of FIG. 1. In various embodiments, travel assistance system 200 performs the method described in FIG. 1.

The travel assistance system 200 includes a memory 225, storage 230, an interconnect (e.g., BUS) 220, one or more CPUs 205 (also referred to as processors 205 herein), an I/O device interface 210, I/O devices 212, and a network interface 215. Memory 225 can comprise instructions 255. Storage 230 can comprise a traveler profile 260 and destination profile 265. Travel assistance system 200 can further be coupled to a network 235, database 240, wearables 245 and end user device 250.

Each CPU 205 retrieves and executes programming instructions stored in the memory 225 or storage 230. The interconnect 220 is used to move data, such as programming instructions, between the CPUs 205, I/O device interface 210, storage 230, network interface 215, and memory 225. The interconnect 220 can be implemented using one or more busses. The CPUs 205 can be a single CPU, multiple CPUs, or a single CPU having multiple processing cores in various embodiments. In some embodiments, a CPU 205 can be a digital signal processor (DSP). In some embodiments, CPU 205 includes one or more 3D integrated circuits (3DICs) (e.g., 3D wafer-level packaging (3DWLP), 3D interposer based integration, 3D stacked ICs (3D-SICs), monolithic 3D ICs, 3D heterogeneous integration, 3D system in package (3DSiP), and/or package on package (PoP) CPU configurations). Memory 225 is generally included to be representative of a random access memory (e.g., static random access memory (SRAM), dynamic random access memory (DRAM), or Flash). The storage 230 is generally included to be representative of the cloud or other devices connected to the travel assistance system 200 via the I/O devices interface 210 or a network 235 via the network interface 215. In embodiments, network 235 can be configured to perform similar to the network system comprised in operation 110.

In some embodiments, the memory 225 stores instructions 255 and the storage 230 stores traveler profile 260 and destination profile 265. In embodiments, storage 230 can be a repository residing on highly-replicated backend storage systems distributed geographically across a plurality of devices 245. In embodiments, the plurality of devices can comprise medical wearables and handhelds (e.g., smartwatches, smart shoes, smart glasses, and hearing aids) and connected devices. Health data stored on the plurality of devices is extracted and uploaded to traveler profile 260. Instructions 255 initiates data collection comprising, but not limited to, heart rate, calories burned, steps walked, blood pressure, and fitness level of traveling individuals and family members. Connected devices are the associated data sources comprised throughout individual and group members in a traveling party. Connected devices 230 can comprise mobile devices, tablets, and computers. Information collected throughout connected devices can comprise medical records preferences of the individual and group members of the traveling party. Medical records data can comprise a traveler's medical history portfolio and preferences can comprise biological and psychological data. Information from connected devices can be taken from, for example, social media posts, web browsing history, and unrestricted emails.

Traveler profile 260 can be consistent with the personal and group profiles established in operation 120 and operation 130 of FIG. 1. Traveler profile 260 can further store, for example, health information relative to a traveler collected from database 240 via network 235.

Destination profile 265 can be consistent with the vacation destination profiles built in operation 150 of FIG. 1. Destination profile 265 can store a plurality of related data for potential travel destinations collected from database 240. Database 240 comprises analytics from a plurality of geological databases, such as, for example, travel locations, hyper-local data, location insights, global weather data, and weather broadcast stations to establish potential factors for destination profiles. Database 240 is connected to travel assistance system 200 via network 235.

Instructions 255 are processor executable instructions including rules and commands for updating and selecting the highest compatibility mapped score across traveler profile 260 and destination profile 265 considering all factors derived in method 100. Instructions 255 can be executed by travel assistance system 200 to collect data from numerous devices in an IoT environment and generate a highly compatible travel itinerary based on the collected data. The travel itinerary is output to end user device 250.

In various embodiments, the I/O devices 212 include an interface capable of presenting information and receiving input (e.g., user interface 138 of FIG. 1).

FIG. 2 is intended to represent components of an example travel assistance system 200 according to embodiments of the present disclosure. In some embodiments, however, individual components can have greater or lesser complexity than shown in FIG. 2, and components other than, or in addition to those shown in FIG. 2 can be present. Furthermore, in some embodiments, various components illustrated in FIG. 2 can have greater, lesser, or different functionality than shown in FIG. 2.

Figure 3:
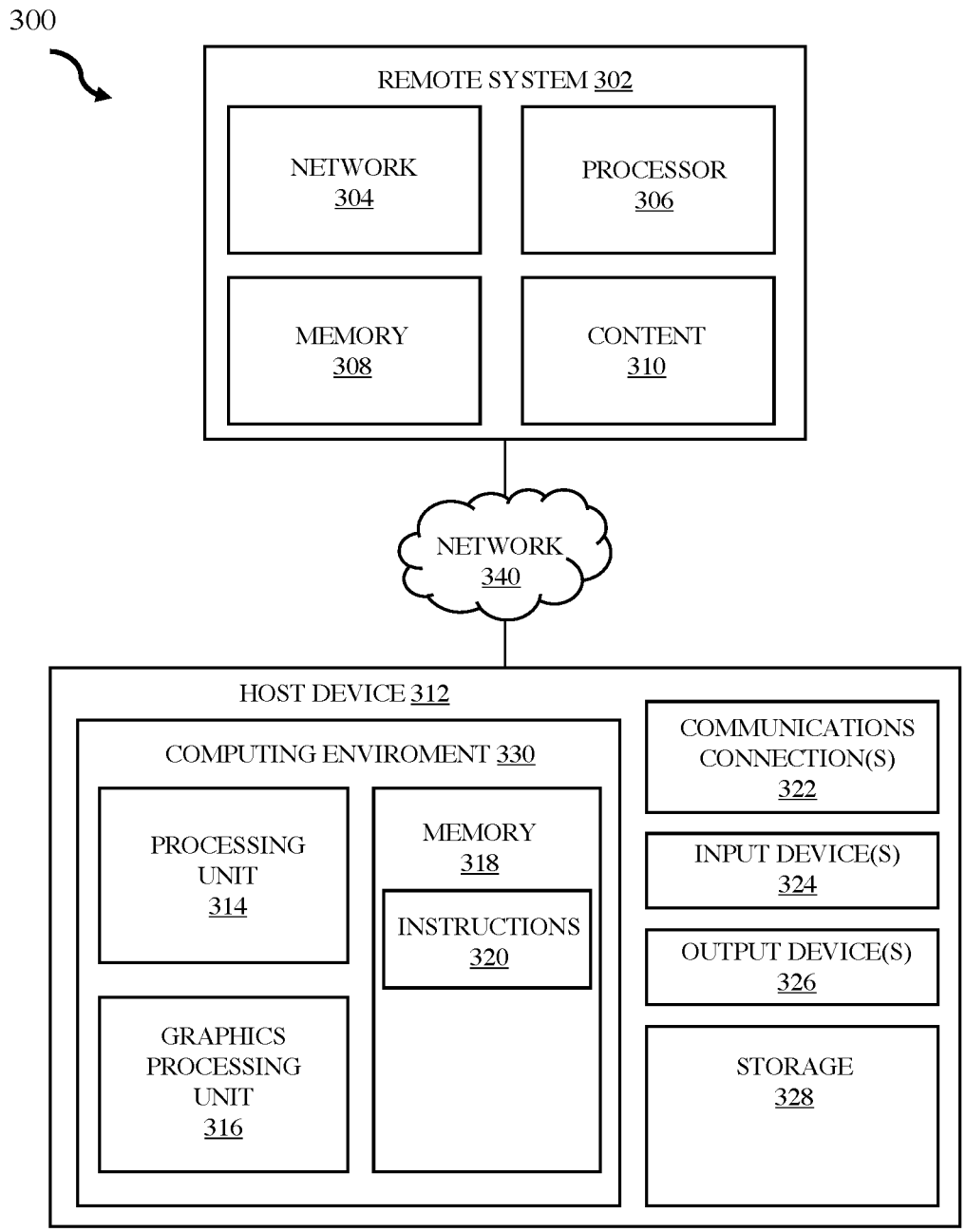
FIG. 3 illustrates a block diagram of an example instruction-based computing environment in accordance with some embodiments of the present disclosure.

FIG. 3 depicts a block diagram of an example computing environment 300 in which embodiments of the present disclosure can be implemented. In some embodiments, aspects of computing environment 300 can perform the methods described in FIG. 1. In embodiments, the computing environment 300 can include a remote system 302 and a host device 312.

According to embodiments, the host device 312 and the remote system 302 can be computer systems. The remote system 302 and the host device 312 can include one or more processors 306 and 314 and one or more memories 308 and 318, respectively. The remote system 302 and the host device 312 can be configured to communicate with each other through an internal or external network interface 304 and communications connection(s) 320 (e.g., modems or interface cards). The remote system 302 and/or the host device 312 can be equipped with a display or monitor. Additionally, the remote device 302 and/or the host device 312 can include optional input devices (e.g., a keyboard, mouse, scanner, or other input device), and/or any commercially available or custom software (e.g., browser software, communications software, server software, natural language processing software, search engine, and/or web crawling software, filter modules for filtering content based upon predefined parameters, etc.). In some embodiments, the remote system 302 and/or the host device 312 can be servers, desktops, laptops, or hand-held devices.

The remote system 302 and the host device 312 can be distant from each other and can communicate over a network 340. Network 340 can be consistent with network 235 of FIG. 2. In embodiments, the host device 312 can be a central hub from which a remote system 302 and other remote devices (not pictured) can establish a communication connection, such as in a client-server networking model. In some embodiments, the host device 312 and remote system 302 can be configured in any other suitable network relationship (e.g., in a peer-to-peer configuration or using another network topology).

In embodiments, the network 340 can be implemented using any number of any suitable communications media. For example, the network 340 can be a wide area network (WAN), a local area network (LAN), the Internet, or an intranet. In certain embodiments, the remote system 302 and the host device 312 can be local to each other and communicate via any appropriate local communication medium. For example, the remote system 302 and the host device 312 can communicate using a local area network (LAN), one or more hardwire connections, a wireless link or router, or an intranet. In some embodiments, the remote system, the host device 312, and any other devices can be communicatively coupled using a combination of one or more networks and/or one or more local connections. For example, the remote system 302 can be hardwired to the host device 312 (e.g., connected with an Ethernet cable) while a second device (not pictured) can communicate with the host device using the network 340 (e.g., over the Internet).

In some embodiments, the network 340 can be implemented within a cloud computing environment or using one or more cloud computing services. Consistent with various embodiments, a cloud computing environment can include a network-based, distributed data processing system that provides one or more cloud computing services. Further, a cloud computing environment can include many computers (e.g., hundreds or thousands of computers or more) disposed within one or more data centers and configured to share resources over the network 340.

In some embodiments, the remote system 302 can enable users to provide health information to the host device 312. In some embodiments, the host device 312 can include input device(s) 324 and output device(s) 326 directly. The host device 312 can contain subcomponents, such as a computing environment 330. The computing environment 330 can include a processing unit 314, a graphics processing unit 316, and a memory 318. Memory 318 comprises instructions 320. In embodiments, instructions 320 can be consistent with instructions 255 of FIG. 2. The computing environment 330 can be configured to perform processing to ingest content 310 from remote system 302. In various embodiments, content 310 can further comprise other health information, images, a set of data (e.g., a user profile), or a corpus of data (e.g., a database of patient profiles, symptoms, etc.).

The storage 328 can be configured to store training information regarding weighted data as well as can be connected to memory 318. Storage 328 can be consistent with storage 230 of FIG. 2.

While FIG. 3 illustrates a computing environment 300 with a single host device 312 and a single remote system 302, suitable computing environments for implementing embodiments of this disclosure can include any number of remote devices and host devices. The various models, modules, systems, instructions, and components illustrated in FIG. 3 can exist, if at all, across a plurality of host devices and remote devices.

It is noted that FIG. 3 is intended to depict the representative major components of an example computing environment 300. In some embodiments, however, individual components can have greater or lesser complexity than as represented in FIG. 3, components other than or in addition to those shown in FIG. 3 can be present, and the number, type, and configuration of such components can vary.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
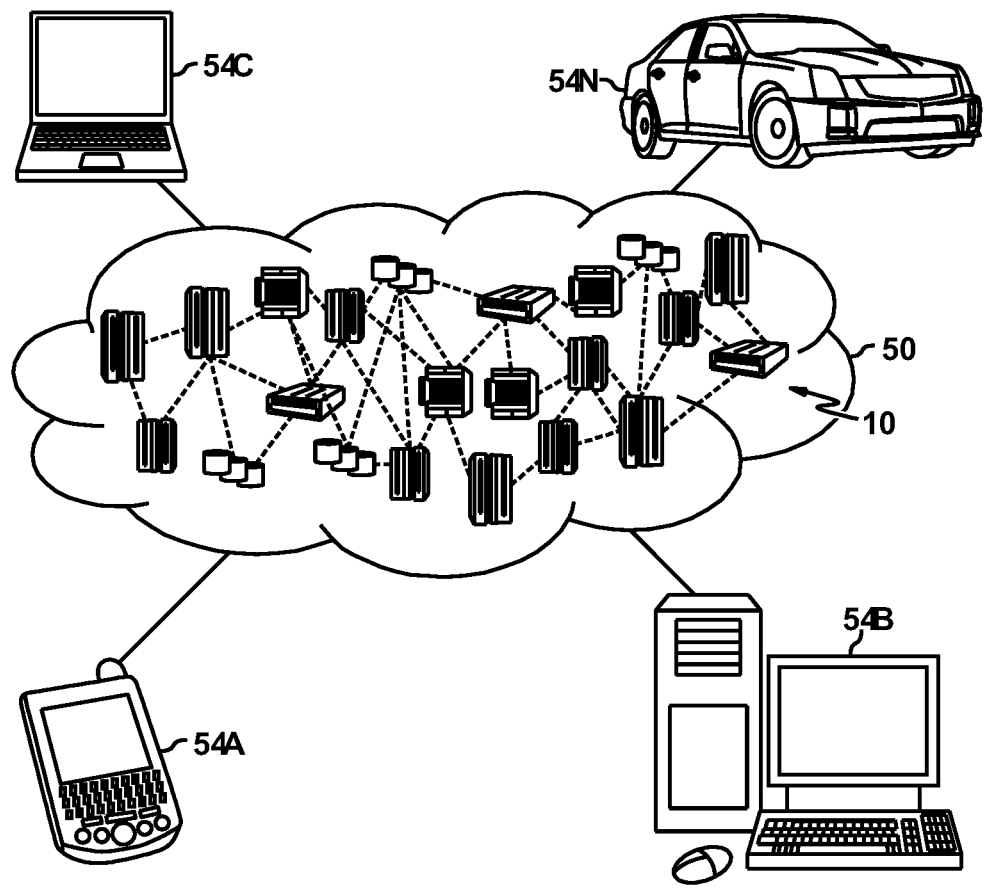
FIG. 4 depicts a cloud computing environment according to an embodiment of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 5:
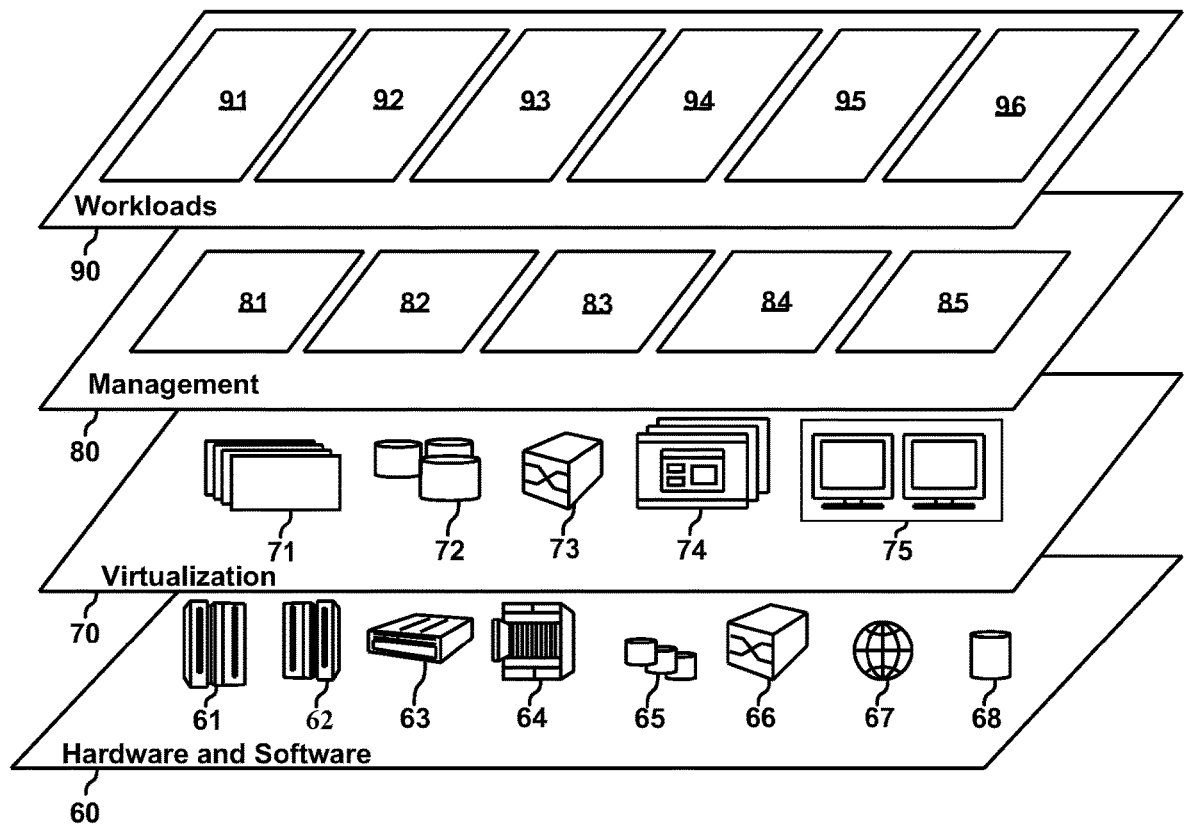
FIG. 5 depicts abstraction model layers according to an embodiment of the present invention.

Referring now to FIG. 5, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and travel assistance 96.

Embodiments of the present invention may be a system, a method, and/or a computer program product at any possible technical detail level of integration. The computer program product may include a computer readable storage medium (or media having computer readable program instructions thereon for causing the processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or subset of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While it is understood that the process software may be deployed by manually loading it directly in the client, server, and proxy computers via loading a storage medium such as a CD, DVD, etc., the process software may also be automatically or semi-automatically deployed into a computer system by sending the process software to a central server or a group of central servers. The process software is then downloaded into the client computers that will execute the process software. Alternatively, the process software is sent directly to the client system via e-mail. The process software is then either detached to a directory or loaded into a directory by executing a set of program instructions that detaches the process software into a directory. Another alternative is to send the process software directly to a directory on the client computer hard drive. When there are proxy servers, the process will select the proxy server code, determine on which computers to place the proxy servers' code, transmit the proxy server code, and then install the proxy server code on the proxy computer. The process software will be transmitted to the proxy server, and then it will be stored on the proxy server.

Embodiments of the present invention may also be delivered as part of a service engagement with a client corporation, nonprofit organization, government entity, internal organizational structure, or the like. These embodiments may include configuring a computer system to perform, and deploying software, hardware, and web services that implement, some or all of the methods described herein. These embodiments may also include analyzing the client's operations, creating recommendations responsive to the analysis, building systems that implement subsets of the recommendations, integrating the systems into existing processes and infrastructure, metering use of the systems, allocating expenses to users of the systems, and billing, invoicing, or otherwise receiving payment for use of the systems.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method to generate and recommend an optimized vacation or travel destination and itinerary, the method comprising:
   combining one or more real-time data sources associated with a plurality of travelers, wherein real-time data sources comprise wearables and connected devices, wherein the combining comprises:
   receiving a plurality of data, wherein a first portion of the plurality of data is associated with a first classification, a second portion of the plurality of data is associated with a second classification, and a third portion of the plurality of data is associated with a third classification, wherein the plurality of data comprises health information,
   storing the health information in an isolated database, and extracting traveler information from the isolated database using a machine learning model and natural language processing;

building a personal profile vector for each individual traveler comprised in the plurality of travelers by using a k-means clustering algorithm;

building a group profile vector from the individual travelers comprised in the plurality of travelers by clustering;

retrieving travel destinations and environmental forecast factors;

building destination profiles by:
 mapping the dimensional compatibility of potential destinations to the group profile vector wherein mapping comprises evaluating like dimensions, wherein overlaying dimensions are assigned a value of 1 and misaligned dimensions are assigned a value of 0, wherein a mapped score ranges from a number of proposed dimensions and each mapped destination is given a monthly score;

outputting a recommended vacation or travel destination and itinerary to the one or more data source, wherein an optimized travel itinerary comprises a report for the highest map-scored destination, travel method, and travel date, wherein a report further comprises a recommended packing list and potential surprise alternatives based on predictive environmental conditions; and updating dimensions of the group profile vector based on traveler's feedback.

2. The method of claim 1, further comprising, analyzing existing conditions within the plurality of travelers to identify unknown medical conditions and recommend mitigation steps.

3. The method of claim 1, wherein the first portion of the plurality of data comprises health data, wherein the second portion of the plurality of data comprises medical data, and wherein the third portion of the plurality of data comprises biological data.

4. The method of claim 1, wherein the personal profile vectors comprise health services, social media, web-based messages, and devices and dimensions comprise categorical identifiers relating to vital signs, personality, and preferences of the plurality of travelers, wherein dimensions are weighted based on individual or group motivation for selecting a destination.

5. The method of claim 1, wherein environmental forecast factors are predicted from historical weather and geographical data analysis.

6. A system to generate and recommend an optimized vacation or travel destination and itinerary, the system comprising:
 a computer readable storage medium storing a corpus of data;
 a user interface configured to receive input and present output; and
 a processor communicatively coupled to the computer readable storage medium and the user interface and having a memory comprising instructions, which, when executed by the processor, cause the processor to:
 combine one or more real-time data sources associated with a plurality of travelers, wherein real-time data sources comprise wearables and connected devices, wherein the combining comprises:
  receiving a plurality of data, wherein a first portion of the plurality of data is associated with a first classification, a second portion of the plurality of data is associated with a second classification, and a third portion of the plurality of data is associated with a third classification, wherein the plurality of data comprises health information, storing the health information in an isolated database, and extracting traveler information from the isolated database using a machine learning model and natural language processing;

build a personal profile vector for each individual traveler comprised in the plurality of travelers by using a k-means clustering algorithm;

build a group profile vector from the individual travelers comprised in the plurality of travelers by clustering;

retrieve travel destinations and environmental forecast factors;

build destination profiles by:
  mapping the dimensional compatibility of potential destinations to the group profile vector, wherein overlaying dimensions are assigned a value of 1 and misaligned dimensions are assigned a value of 0, wherein a mapped score ranges from a number of proposed dimensions and each mapped destination is given a monthly score;

output a recommended vacation or travel destination and itinerary to the one or more data source, wherein an optimized travel itinerary comprises a report for the highest map-scored destination, travel method, and travel date, wherein a report further comprises a recommended packing list and potential surprise alternatives based on predictive environmental conditions; and update dimensions of the group profile vector based on traveler's feedback.

7. The system of claim 6, further comprising, analyzing existing conditions within the plurality of travelers to identify unknown medical conditions and recommend mitigation steps.

8. The system of claim 6, wherein the first portion of the plurality of data comprises health data, wherein the second portion of the plurality of data comprises medical data, and wherein the third portion of the plurality of data comprises biological data.

9. The system of claim 6, wherein the personal profile vectors comprise health services, social media, web-based messages, and devices and dimensions comprise categorical identifiers relating to vital signs, personality, and preferences of the plurality of travelers, wherein dimensions are weighted based on individual or group motivation for selecting a destination.

10. The system of claim 6, wherein environmental forecast factors are predicted from historical weather and geographical data analysis.

11. A computer program product for generating and recommending an optimized vacation or travel destination and itinerary, the computer program product comprising a computer readable storage medium having program instructions embodied therewith, the program instructions executable by a processor to cause the processor to:
 combining one or more real-time data sources associated with a plurality of travelers, wherein real-time data sources comprise wearables and connected devices, wherein the combining comprises:
  receiving a plurality of data, wherein a first portion of the plurality of data is associated with a first classification, a second portion of the plurality of data is associated with a second classification, and a third portion of the plurality of data is associated with a third classification, wherein the plurality of data comprises health information,
storing the health information in an isolated database, and
extracting traveler information from the isolated database using a machine learning model and natural language processing;
building a personal profile vector for each individual traveler comprised in the plurality of travelers by using a k-means clustering algorithm;
building a group profile vector from the individual travelers comprised in the plurality of travelers by clustering;
retrieving travel destinations and environmental forecast factors;
building destination profiles by:
mapping the dimensional compatibility of potential destinations to the group profile vector, wherein overlaying dimensions are assigned a value of 1 and misaligned dimensions are assigned a value of 0, wherein a mapped score ranges from a number of proposed dimensions and each mapped destination is given a monthly score;
outputting a recommended vacation or travel destination and itinerary to the one or more data source, wherein an optimized travel itinerary comprises a report for the highest map-scored destination, travel method, and travel date, wherein a report further comprises a recommended packing list and potential surprise alternatives based on predictive environmental conditions; and
updating dimensions of the group profile vector based on traveler's feedback.

12. The computer program product of claim 11, wherein the first portion of the plurality of data comprises health data, wherein the second portion of the plurality of data comprises medical data, and wherein the third portion of the plurality of data comprises biological data.

* * * * *